US006235031B1

(12) United States Patent
Hodgeman et al.

(10) Patent No.: US 6,235,031 B1
(45) Date of Patent: May 22, 2001

(54) INTRAMEDULLARY FRACTURE FIXATION DEVICE

(75) Inventors: John D. Hodgeman; Stephen C. Roy, both of Boca Raton, FL (US)

(73) Assignee: Encore Medical Corporation, Austin, TX (US)

( * ) Notice: Subject to any disclaimer, the term of this patent is extended or adjusted under 35 U.S.C. 154(b) by 0 days.

(21) Appl. No.: 09/497,530

(22) Filed: Feb. 4, 2000

(51) Int. Cl.[7] .................................................. A61B 17/72
(52) U.S. Cl. ................................................................ 606/64
(58) Field of Search ........................................ 606/62, 64

(56) References Cited

U.S. PATENT DOCUMENTS

| 3,433,220 |   | 3/1969  | Zickel .           |        |
|-----------|---|---------|--------------------|--------|
| 4,432,358 |   | 2/1984  | Fixel .            |        |
| 4,438,762 |   | 3/1984  | Kyle .             |        |
| 4,621,629 |   | 11/1986 | Koeneman .         |        |
| 4,622,959 |   | 11/1986 | Marcus .           |        |
| 4,657,001 |   | 4/1987  | Fixel .            |        |
| 4,667,664 |   | 5/1987  | Taylor et al. .    |        |
| 4,697,585 |   | 10/1987 | Williams .         |        |
| 4,733,654 |   | 3/1988  | Marino .           |        |
| 4,733,664 |   | 3/1988  | Kirsch et al. .    |        |
| 4,776,330 |   | 10/1988 | Chapman et al. .   |        |
| 4,805,607 |   | 2/1989  | Engelhardt et al. .|        |
| 4,827,917 |   | 5/1989  | Brumfield .        |        |
| 5,032,125 |   | 7/1991  | Durham et al. .    |        |
| 5,176,681 |   | 1/1993  | Lawes et al. .     |        |
| 5,312,406 | * | 5/1994  | Brumfield ........................ | 606/64 |
| 5,454,813 |   | 10/1995 | Lawes .            |        |
| 5,531,748 | * | 7/1996  | De La Caffiniere ............... | 606/62 |
| 6,123,708 | * | 9/2000  | Kilpela et al. .................. | 606/64 X |
| 6,126,661 | * | 10/2000 | Faccioli et al. .................. | 606/64 |

FOREIGN PATENT DOCUMENTS 0 321 170 A1    6/1989    (EP) .
2 209 947       6/1989    (GB) .

OTHER PUBLICATIONS

Alta IM Rod Module, Alta "Modular Trama System", May 1990.

The Gamma Locking Nail, (Howmedica) "Lag Screw Compression and Dynamic Osteosynthesis" (No Date).

Operating Guide, Howmedica Trauma, Trochanteric Gamma® Locking Nail, Surgical technique for femoral fracture fixation, pp. 4, 6 and 7, Circa 1998.

* cited by examiner

Primary Examiner—Jeffrey A. Smith
(74) Attorney, Agent, or Firm—Bacon & Thomas, PLLC

(57) ABSTRACT

An intramedullary fracture fixation device is provided which includes an intramedullary rod, a lag screw and a lag screw collar. The rod has a proximal end with a transverse bore extending therethrough. The lag screw has a distal end with coarse bone engaging thread elements and a proximal end with screw threads. When in use, the lag screw is substantially axially aligned with the transverse bore of the rod. The lag screw collar has an outer diameter sized to rotatably fit within the transverse bore of the rod. The collar also has an inner diameter and internal screw threads adapted to cooperate with the screw threads of the proximal end of the lag screw. The lag screw collar may have an increased outer diameter at one end thereof which is at least slightly larger than a diameter of the transverse bore of the rod. The device preferably includes a longitudinal bore which extends through the proximal end of the rod so as to open into the transverse bore. The longitudinal bore is preferably angularly offset with respect to a longitudinal axis of the proximal end of the rod. The device also preferably includes a set screw which is adapted to be secured within the longitudinal bore of the rod with a distal end thereof extending at least partially into the transverse bore of the rod so as to engage the collar when the collar is disposed within the transverse bore.

20 Claims, 4 Drawing Sheets

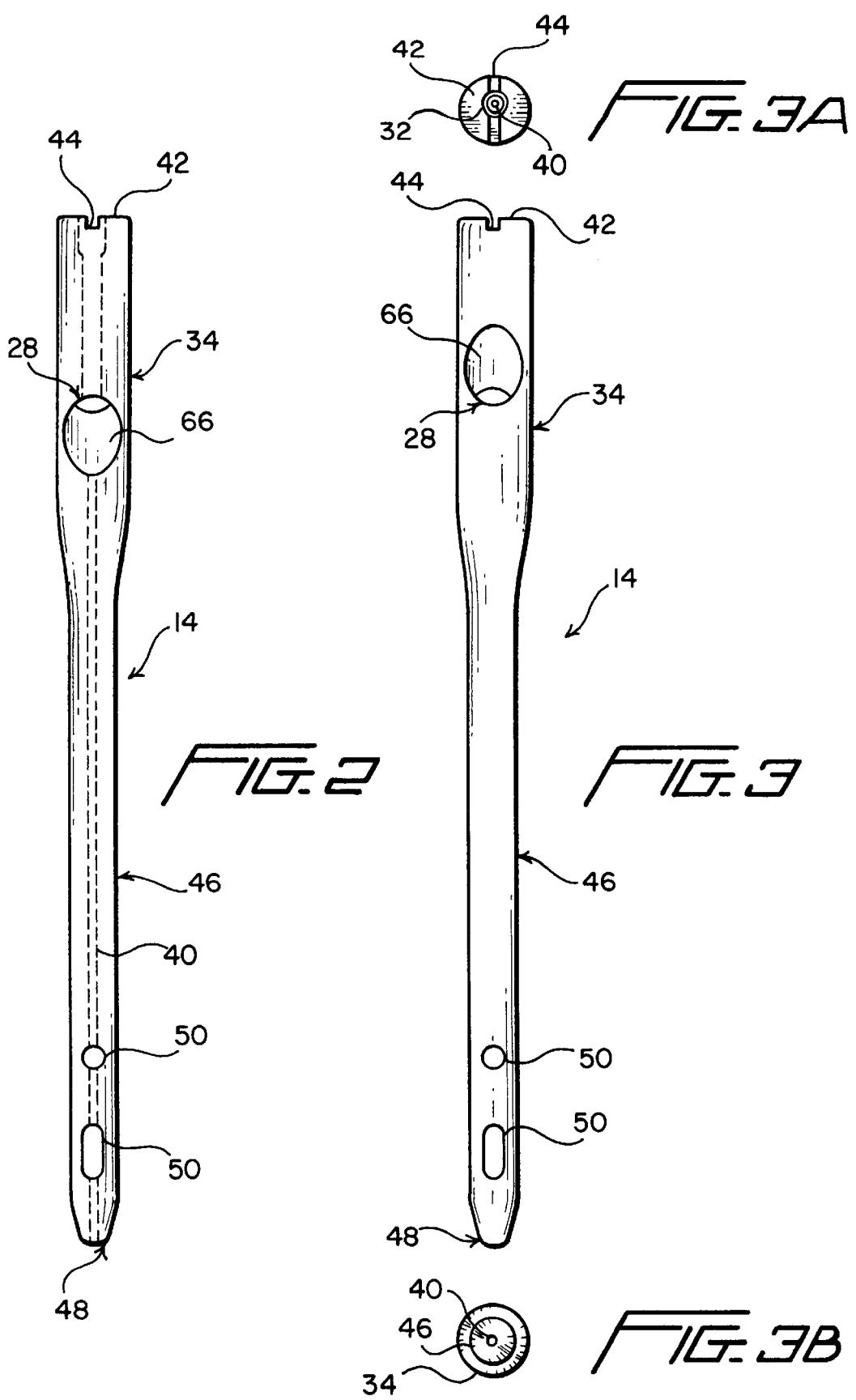

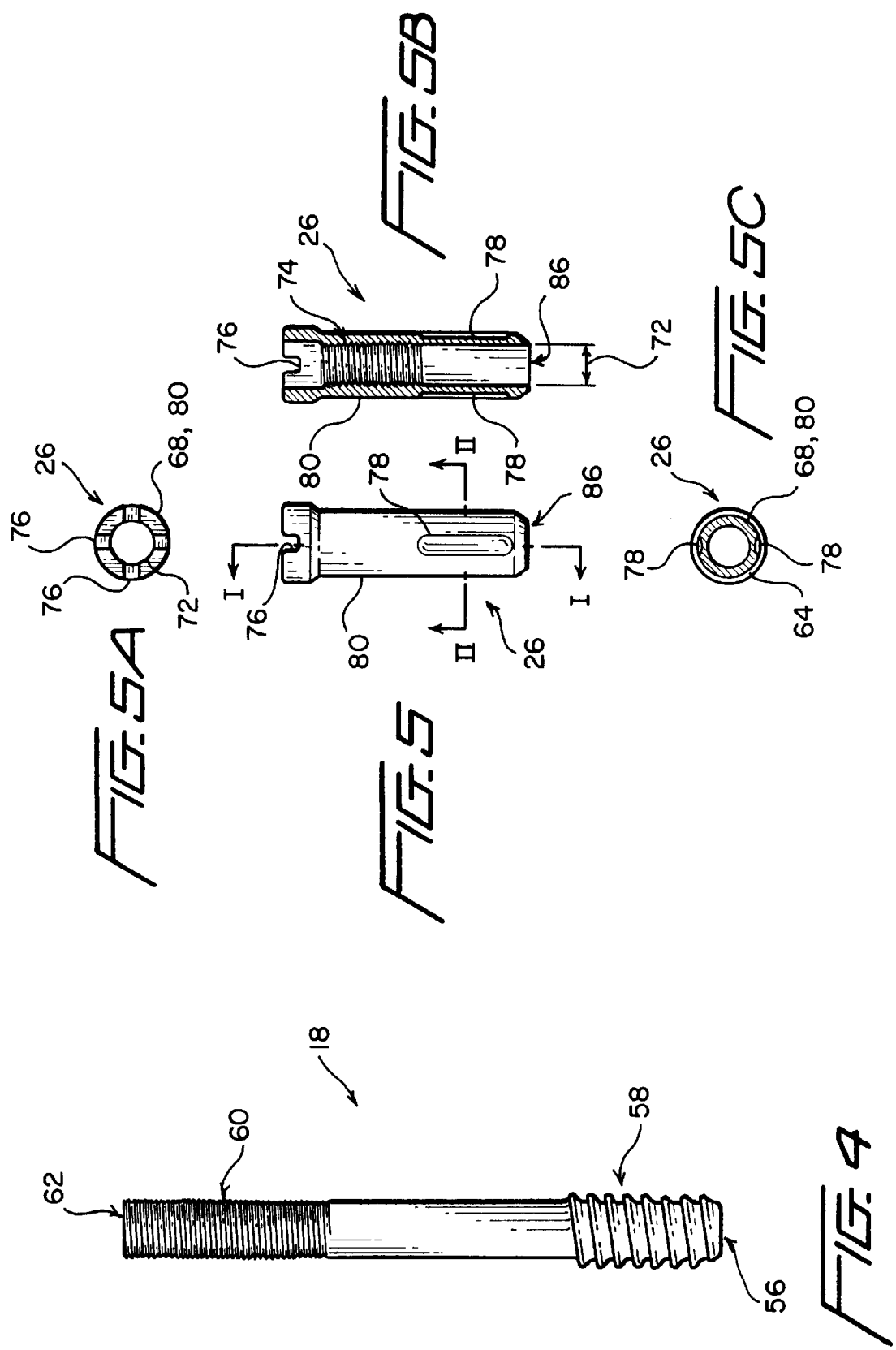

INTRAMEDULLARY FRACTURE FIXATION DEVICE

BACKGROUND OF THE INVENTION

1. Field of the Invention

The present invention relates to an intramedullary fracture fixation device. More specifically, the present invention relates to such a device for fixation of fractures of the proximal femur, including intertrochanteric and subtrochanteric fractures.

2. Description of the Related Art

A variety of fracture fixation devices are known for treatment of femoral fractures. In particular, intramedullary devices are known which provide distinct advantages over known nail-plate combination devices, especially for subtrochanteric and femoral shaft fractures. A good background discussion of such an intramedullary (IM) rod and cross-nail (lag screw) assembly is provided by U.S. Pat. No. 3,433,220 issued to Zickel, which is herein incorporated by reference in its entirety.

Known intramedullary devices have also been designed for treatment of intertrochanteric and femoral neck fractures. For example, U.S. Pat. No. 4,827,917 issued to Brumfield and U.S. Pat. No. 5,032,125 issued to Durham et al., which are herein incorporated by reference in their entirety, each disclose an intramedullary device having an IM rod, a lag screw, a set screw. Additionally, the device of Durham et al. includes a sleeve and a compression screw.

A further excellent description of an intramedullary device similar to that of the present application is set forth in the published United Kingdom Patent Application 2 209 947 A, which again is herein incorporated by reference in its entirety. This reference discloses a basic assembly of an IM rod, a lag screw and a set screw.

The disclosures of all three of the above references are considered to establish the state of the art. Each of the devices disclosed thereby address the desirability of compression in the treatment of femoral fractures and particularly emphasize sliding compression.

Brumfield teaches a lag screw which has a threaded portion and a smooth portion. The threaded portion is at a distal end to be screwed into the femoral head. The smooth portion is provided intermediate the threaded distal end and a head portion. The lag screw is installed into an angled/inclined bore in the IM rod and screwed into the femoral head. The smooth portion of the screw slides within the bore such that the head portion abuts an outer cortex of the bone to provide the desired sliding compression.

Durham et al. teaches a lag screw, sleeve and compression screw combination for achieving sliding compression. The sleeve is designed to fit within the angled bore of the IM rod with a proximal end of the lag screw extending into the sleeve. Both the sleeve and the lag screw are "keyed" to prevent the lag screw from rotating within the sleeve while permitting the lag screw to slide within the sleeve. The proximal end of the lag screw has an internally threaded bore for receiving the compression screw, which is correspondingly threaded. The compression screw is screwed into the proximal end of the lag screw so as to slide the lag screw relative to the sleeve to provide the desired sliding compression.

UK 2 209 947 A teaches the use of a tool which puts a traction force on the lag screw in a direction away from the femoral head. Although not explained in detail, the tool abuts a sleeve which is placed temporarily on the outer cortex of the femoral shaft.

SUMMARY OF THE INVENTION

It is an object of the present invention to provide an intramedullary fracture fixation device for fixation of fractures of the proximal femur which overcomes certain disadvantages of the prior art devices while maintaining their advantages. The present invention aims to simplify and improve the manner of achieving desired compression. The invention also aims to provide increased flexibility in surgical applications of the device while reduce manufacturing costs thereof. In order to meet this object, the present invention has been developed with various unique and patentable features as described hereinafter.

According to one embodiment of the present invention, the intramedullary fracture fixation device comprises an intramedullary rod, a lag screw and a lag screw collar. The rod has a proximal end with a transverse bore extending therethrough. The lag screw has a distal end with having course bone engaging thread elements and a proximal end with screw threads. When in use, the lag screw is substantially axially aligned with the transverse bore of the rod. The lag screw collar has an outer diameter sized to rotatably fit within the transverse bore of the rod. The collar also has an inner diameter and internal screw threads adapted to cooperate with the screw threads of the proximal end of the lag screw.

According to a second embodiment, the intramedullary fracture fixation device also comprises an intramedullary rod, a lag screw and a lag screw collar. The rod has a proximal end with a transverse bore extending therethrough. The lag screw has a distal end with having coarse bone-engaging thread elements and a proximal end with screw threads. When in use, the lag screw is substantially axially aligned with the transverse bore of the rod. The lag screw collar has an outer diameter over at least a portion thereof which is sized to rotatably fit within the transverse bore of the rod and an increased outer diameter at one end thereof which is at least slightly larger than a diameter of the transverse bore of the rod. The collar also has an inner diameter and internal screw threads adapted to cooperate with the screw threads of the proximal end of the lag screw.

According to a variant of the above embodiments, the outer diameter of the collar is preferably sized to substantially abut an inner wall of the transverse bore of the rod such that the collar acts as a centering device for the lag screw relative to the transverse bore.

Further, the collar preferably includes at least one flattened outer engagement surface or at least one engagement groove formed on an outer surface thereof.

Still further, the above embodiments may further comprise a longitudinal bore which extends through the proximal end of the rod so as to open into the transverse bore. The longitudinal bore is preferably angularly offset with respect to a longitudinal axis of the proximal end of the rod.

According to a third embodiment, the intramedullary fracture fixation device comprises an intramedullary rod with both transverse and longitudinal bores. The transverse bore extends through a proximal end of the rod. The longitudinal bore extends through the proximal end of the rod so as to open into the transverse bore. The longitudinal bore is angularly offset with respect to a longitudinal axis of the proximal end of the rod.

According to a variant of the third embodiment, the device further comprises a collar and a set screw. The collar preferably has an outer diameter sized to fit within the transverse bore of the rod. The set screw is preferably adapted to be secured within the longitudinal bore of the rod with a distal end thereof extending at least partially into the transverse bore of the rod so as to engage the collar when the collar is disposed within the transverse bore.

Further, the collar preferably includes at least one flattened outer engagement surface or at least one engagement groove formed on an outer surface thereof. In such case, the set screw is adapted to engage the engagement surface or groove so as to prevent rotation of the collar within the transverse bore of the rod.

BRIEF DESCRIPTION OF THE DRAWINGS

Other features as well as the advantages of the present invention will be better understood upon reading the following detailed description of the preferred embodiments with reference to the accompanying drawings, in which:

FIG. 2 is a right side view of an embodiment of the intramedullary rod according to the present invention;

FIG. 3 is a left side view of the embodiment of the intramedullary rod of FIG. 2;

FIG. 3A is a top view of the embodiment of the intramedullary rod as shown in FIG. 3;

FIG. 3B is a bottom view of the embodiment of the intramedullary rod as shown in FIG. 3;

FIG. 4 is a plan view of an embodiment of the lag screw according to the present invention;

FIG. 5 is a plan view of an embodiment of the lag screw collar according to the present invention;

FIG. 5A is a top view of the embodiment of the lag screw collar of FIG. 5;

FIG. 5B is a cross-sectional view of the embodiment of the lag screw collar of FIG. 5 taken along section line I—I;

FIG. 5C is a cross-sectional view of the embodiment of the lag screw collar of FIG. 5 taken along section line II—II;

DETAILED DESCRIPTION OF THE PREFERRED EMBODIMENTS

Figure 1:
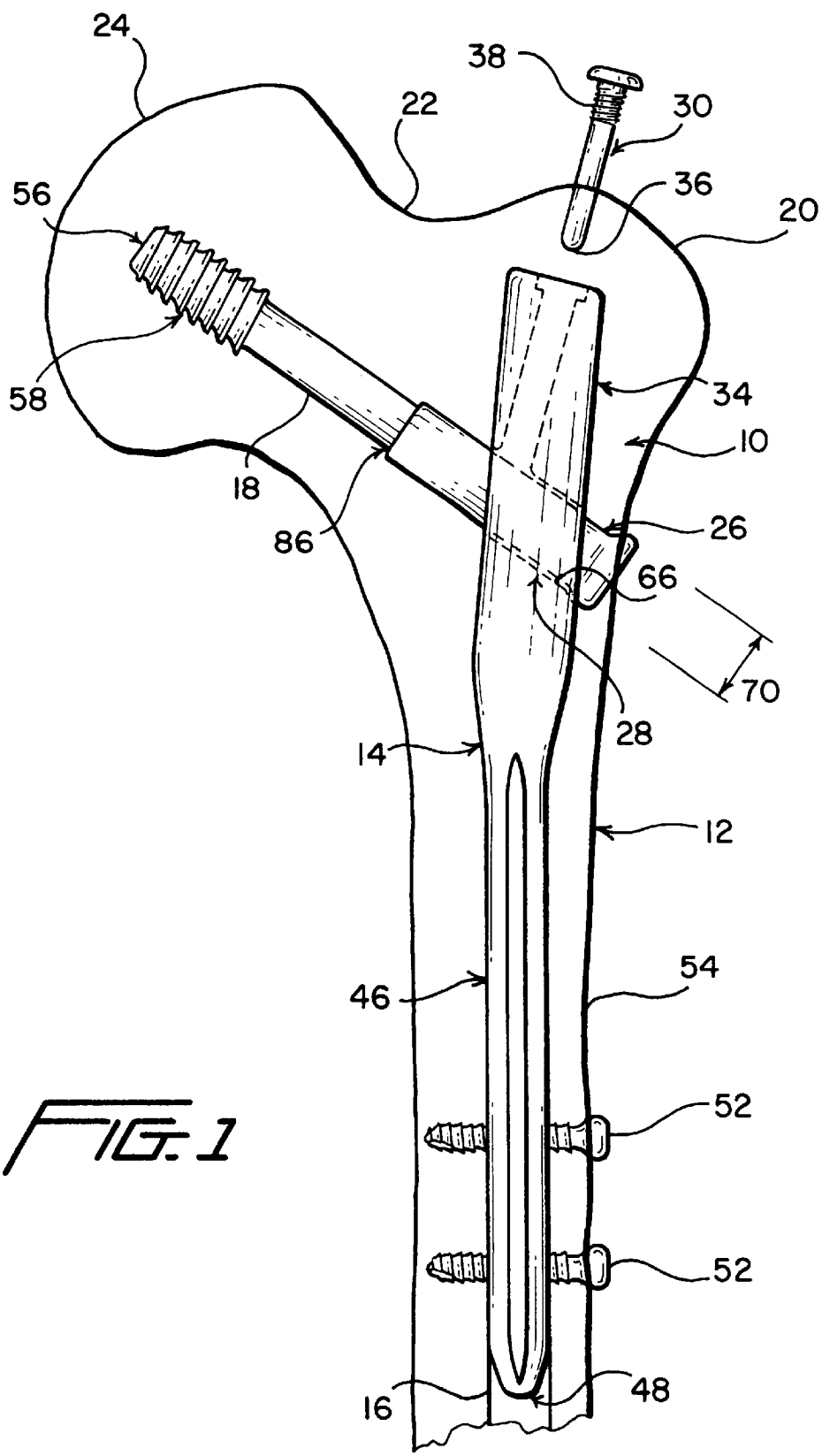
FIG. 1 is a plan view of a preferred embodiment of the present invention as installed for fixation of a fracture of the proximal femur.

As shown in FIG. 1 according to a preferred embodiment of the invention, an intramedullary fracture fixation device 10 is designed to be installed within a fractured human femur 12 in the upper third or subtrochanteric portion thereof. The basic structure includes an IM rod 14 which is installed within the medullary or marrow canal 16 of the femur 12 in accordance with known medical procedures. A lag screw 18 is installed via a hole drilled in or just below the greater trochanter 20 so as to extend though the femoral neck 22 and into the femoral head 24. A lag screw collar 26 is installed coaxially with the lag screw 18 so as to extend into, preferably through, an angled/inclined transverse bore 28 of the IM rod 14. A set screw 30 is installed into a longitudinal bore 32, preferably angularly offset as described below, formed in a proximal end 34 of the IM rod 14.

It should be noted that all parts are preferably manufactured from Titanium Alloy for its optimum strength and proven biocompatibility.

Details of the IM rod 14 will be explained with reference to FIGS. 1, 2, 3, 3A and 3B. As noted above, the proximal end 34 of the IM rod 14 has the angled/inclined transverse bore 28 formed therethrough. The angle/inclination of the transverse bore 28 is such that it will be axially aligned with the femoral head 24 when the IM rod 14 is properly positioned in the medullary canal 16.

Also noted above, the proximal end 34 of the IM rod 14 has the longitudinal bore 32 formed therein. The longitudinal bore 32 extends into the transverse bore 28 as shown in FIG. 1. The longitudinal bore 32 is angularly offset with respect to a longitudinal axis of the proximal end 34 of the IM rod 14. This provides improved access for insertion of the set screw 30 into the longitudinal bore 32, minimizing soft tissue exposure and damage.

Once inserted into the longitudinal bore 32, the set screw 30 is adapted to be secured therein with at least a tip 36 thereof extending at least partially into the transverse bore 28. Of course, any known means of securing the set screw 30 within the longitudinal bore 32 may be used. However, preferably the set screw 30 is secured in an adjustable manner as with conventional screw threading. In such case, the longitudinal bore 32 and the set screw 30 may be entirely or only partially threaded with cooperating screw threads 38.

The angular offset of the longitudinal bore 32 also decreases the obtuse angle made with the transverse bore 28. Thus, the set screw 30 will be positioned more substantially perpendicular to the lag screw collar 26 installed in the transverse bore 28. This provides a more direct application of force from the set screw 30 to the collar 26 to prevent rotation of the collar 26 within the transverse bore 28 once a desired amount of compression (discussed below) is obtained.

As shown in FIGS. 2 and 3B, the IM rod 14 may include a central longitudinal channel 40 throughout its length. As shown in FIGS. 2, 3 and 3A, a butt end 42 of the proximal end 34 of the IM rod 14 may include a transverse slot 44. Transverse slot 44 may be used with an appropriate tool to rotate and/or drive the IM rod 14 into position within the medullary canal 16. It may also be used as a visual or physical guide to ensure that the IM rod is rotated properly so that the transverse bore 28 is axially aligned with the femoral head 24. Aside from any visual indicator, the transverse slot 44 may be tapered or have one end wider than the other to indicate which direction the angle/inclination of the transverse bore 28 is facing. The appropriate tool would then be adapted to fit the transverse slot 44 in only one orientation.

Although actual dimensions will vary to accommodate a variety of clinical needs, the geometry of the IM rod 14 preferably incorporates several unique features for improved fit and fixation. The IM rod 14 preferably includes a series of diameter reduction steps resulting in geometrical "normalizations" to improve the fit transitioning from the metaphysis to the diaphysis regions. The steps provide resistance to axial loads while transferring stress in the fracture region and minimizing stress in the distal region.

As illustrated in the Figures, the IM rod 14 tapers towards a distal end 46 thereof into its designated diameter. This improves the metaphyseal fit. The IM rod 14 is preferably provided to medical practitioners in several different designated diameters, such as 9 mm, 11 mm and 13 mm, to provide improved diaphyseal fit and fixation. The diameter of the proximal end 34 of the IM rod 14 is preferably fixed at about 17.5 mm. This ensures that the IM rod 14 will be compatible for use with the same lag screw 18, collar 26 and set screw 30 regardless of the other dimension of the IM rod 14 so as to minimize inventory for medical practitioners and to simplify assembly of proper elements.

The geometrical "normalizations" of the steps and the multiple diameter options give the IM rod 14 a universal design. As such, there is no need for a medical practitioner to select a left rod or a right rod for proper fit and fixation. This also minimizes inventory for medical practitioners.

The IM rod 14 preferably incorporates a 5 degree mediolateral bend between the proximal end 34 and the distal end 46. This facilitates insertion of the IM rod 14 through the greater trochanter 20. Further, the IM rod 14 preferably has a tapered and radiused tip 48 which minimizes anterior point contact for improved fit. The IM rod 14 may also feature one or more transfixing holes 50 in the distal end 46 for receiving transfixing screws 52 which secure the distal end 46 to the femoral shaft 54. Preferably, a lower one of the transfixing holes 50 is slotted for greater flexibility.

The lag screw 18 is shown in detail in FIG. 4. A distal end 56 thereof is provided with coarse bone-engaging elements 58. The bone-engaging elements 58 are preferably threaded so that the lag screw 18 may be readily secured within the femoral head 24 during use. Screw threads 60 are provided on at least a portion of the lag screw 18 other than the distal end 56. Preferably, the screw threads 60 are provided on a proximal end 62 of the lag screw 18, although they may be provided over the entire remaining length of the lag screw 18. It is important to note, however, that the screw threads 60 must be arranged so that the cooperate with the lag screw collar 26, discussed further below, such that axial movement of the lag screw 18 may be achieved by rotational movement of the collar 26.

One preferred embodiment of the lag screw collar 26 of the invention is shown in FIGS. 5, 5A, 5B and 5C. According to this embodiment, the collar 26 has an outer diameter 64 over at least a portion thereof which is sized to rotatably fit within the transverse bore 28 of the IM rod 14. Preferably, the outer diameter 64 is sized to substantially abut an inner wall 66 of the transverse bore 28. In that case, the collar 26 will act as a centering device for the lag screw 18 relative to the transverse bore 28. Further, the collar 26 has an increased outer diameter 68 at one end thereof which is at least slightly larger than a diameter 70 of the transverse bore 28. As shown in FIG. 5B, the collar 26 has an inner diameter 72 and internal screw threads 74 adapted to cooperate with the screw threads 60 of the lag screw 18.

As shown in FIGS. 5, 5A and 5B, the one end with the increased outer diameter 68 preferably has one or more sets of notches 76. The notches 76 may be designed to cooperate with a screwdriver or similar tool to facilitate insertion and rotation of the collar 26 within the transverse bore 28.

As shown in FIGS. 5, 5B and 5C, the collar 26 preferably includes at least one engagement groove 78 formed on an outer surface 80 thereof. The set screw 30 is adapted to engage the engagement groove 78 when the set screw 30 is secured in the longitudinal bore 32 and the collar 26 is within the transverse bore 28. If more than one engagement groove 78 is provided, they are preferably circumferentially spaced. This will allow proper engagement between the set screw 30 and any one of the engagement grooves 78 as the collar is incrementally rotated.

Figures 6, 6A:
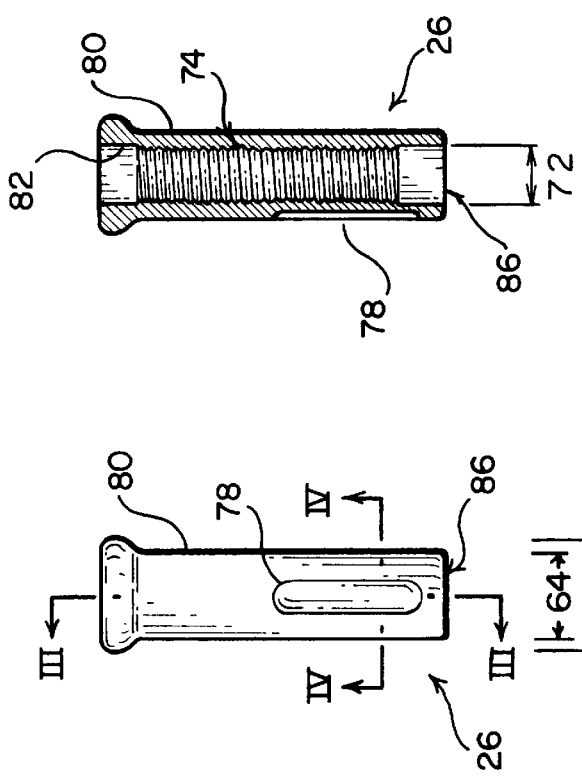
FIG. 6 is a plan view of another embodiment of the lag screw collar according to the present invention.
FIG. 6A is a cross-sectional view of the embodiment of the lag screw collar of FIG. 6 taken along section line III—III, with the engagement groove shown over a greater part of the outer surface of the collar.
Figure 6B:
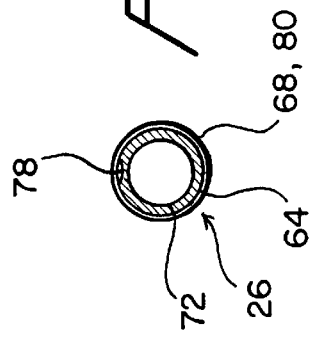
FIG. 6B is a cross-sectional view of the embodiment of the lag screw collar of FIG. 6 taken along section line IV—IV.

Another preferred embodiment of the lag screw collar 26 of the invention is shown in FIGS. 6, 6A and 6B. According to this embodiment, the collar 26 again has the outer diameter 64 over at least a portion thereof which is sized to rotatably fit within the transverse bore 28 of the IM rod 14. Again, the outer diameter 64 may be sized to substantially abut the inner wall 66 of the transverse bore 28 so as to act as a centering device for the lag screw 18 relative to the transverse bore 28. The collar 26 again has the increased outer diameter 68 at one end thereof which is at least slightly larger than the diameter 70 of the transverse bore 28. As shown in FIG. 6A, the collar 26 has the inner diameter 72 and the internal screw threads 74 adapted to cooperate with the screw threads 60 of the lag screw 18.

As shown in FIG. 6A, the one end with the increased outer diameter 68 preferably has a partial bore 82. The partial bore 82 may be designed to cooperate with an Allen wrench or similar tool to facilitate insertion and rotation of the collar 26 within the transverse bore 28.

As shown in FIGS. 6, 6A and 6B, the collar 26 again preferably includes the at least one engagement groove 78 formed on the outer surface 80 thereof. As illustrated by a comparison of FIG. 6 and FIG. 6A, the engagement groove 78 may vary in dimension.

Figures 7, 7A:
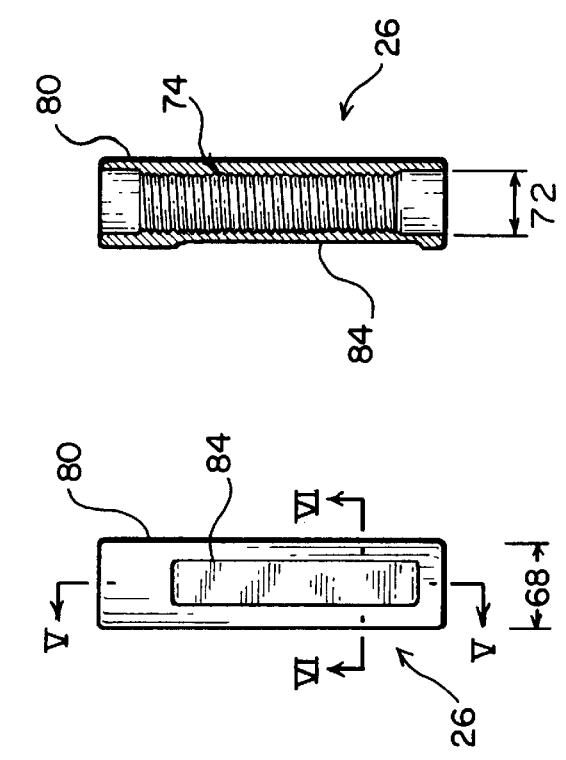
FIG. 7 is a plan view of yet another embodiment of the lag screw collar according to the present invention.
FIG. 7A is a cross-sectional view of the embodiment of the lag screw collar of FIG. 7 taken along section line V—V.
Figure 7B:
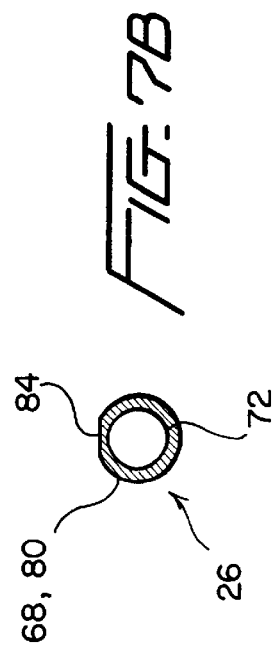
FIG. 7B is a cross-sectional view of the embodiment of the lag screw collar of FIG. 7 taken along section line VI—VI.

A third preferred embodiment of the lag screw collar 26 of the invention is shown in FIGS. 7, 7A and 7B. According to this embodiment, the collar 26 has the outer diameter 64 over the entire length thereof, without the increased outer diameter 68 of the first two embodiments. Again, the outer diameter 64 is sized to rotatably fit within the transverse bore 28 of the IM rod 14 and preferably sized to substantially abut the inner wall 66 of the transverse bore 28. As shown in FIG. 7A, the collar 26 also has the inner diameter 72 and internal screw threads 74 adapted to cooperate with the screw threads 60 of the lag screw 18.

Although neither the notches 76 nor the partial bore 82 are shown for this embodiment, it should be understood that some equivalent structure is preferably included.

As shown in FIGS. 7, 7A and 7B, the collar 26 preferably includes at least one flattened outer engagement surface 84. The set screw 30 is adapted to engage the engagement surface 84 when the set screw 30 is secured in the longitudinal bore 32 and the collar 26 is within the transverse bore 28. As with the engagement grooves 78, if more than one engagement surface 84 is provided, they are preferably circumferentially spaced. Again, this will allow proper engagement between the set screw 30 and any one of the engagement surfaces 84 as the collar is incrementally rotated.

The flattened outer engagement surface 84 provides an advantage over the engagement grooves 78. If after rotation of the collar 26 within the transverse bore 28 the flattened outer engagement surface 84 does not exactly line up with the set screw 30, the tip 36 of the set screw 30 will abut an inclined surface formed by the engagement surface 84. Then, the tip 36 may exert a force on the inclined surface upon rotation of the set screw 30 (in the case of a threaded set screw and threaded longitudinal bore) so that the collar 26 will rotate in an appropriate direction to more substantially align the engagement surface 84 and the set screw 30.

When the first two embodiments of the collar 26 are used, compression is achieved in conjunction with the lag screw 18. The increased diameter 68 of the collar 26 is caused to abut the IM rod 14, as shown in FIG. 1. Alternatively, if a hole having a diameter the size of the outer diameter 64 of the collar 26, but less than the increased diameter 68, is drilled in or just below the greater trochanter 20, then the increased diameter 68 of the collar 26 is caused to abut the outer cortex of the femur. In either case, the collar 26 is rotated within the transverse bore 28 such that its internal screw threads 74 are threaded upon the screw threads 60 of the lag screw 18. Once the increased diameter 68 of the collar 26 abuts the IM rod 14/the outer cortex of the femur, further rotation of the collar 26 will cause compression. Once a desired compression is achieved, the set screw 30 is secured within the longitudinal bore 32 to engage the collar 26 and prevent further rotation of the collar 26.

When the third embodiment of the collar 26 is used, compression may or may not be achieved in conjunction with the lag screw 18. Since there is no increased diameter 68, the collar 26 will not abut the IM rod 14 or the outer cortex of the femur. Depending on the length of the collar 26, the hole drilled into the femur 12 for insertion of the collar 26 may be to a point beyond the medullary canal 16. In that case, the collar 26 is rotated within the transverse bore 28 such that its internal screw threads 74 are threaded upon the screw threads 60 of the lag screw 18. Once the collar 26 is properly positioned around the lag screw 18 and within the transverse bore 28, the set screw 30 is secured within the longitudinal bore 32 to engage the collar 26 and prevent further rotation of the collar 26. Thus, the collar 26 will not provide compression, but rather only a properly aligned connection between the lag screw 18 and the IM rod 14.

If, however, the hole drilled into the femur 12 for insertion of the collar 26 is only to a point at which it intersects the medullary canal 16, then a distal end 86 of the collar 26 will abut the hard bone of the greater trochanter 20. If the hole drilled into the femur 12 for insertion of the collar 26 is to a point beyond the medullary canal 16, the collar 26 may still abut the hard bone of the femoral neck 22, again depending on the length of the collar 26. In either case, the abutment of the collar 26 against bone, in conjunction with the lag screw 18, will achieve compression.

It should be reasonably clear that any or all of the features of the present invention may be included in a kit provided to a medical practitioner. Since the same lag screw and same set screw will be compatible with any of the collar embodiments and any of the IM rod variations, greater treatment flexibility is achieved without the need for excessive inventory or complexity of assembly. Still further advantages of the present invention should be readily apparent to those of skill in the art based upon the written description provided above.

Although multiple preferred embodiments of the invention have been described above, it is to be understood that various modifications could be made to the embodiments by any person skilled in the art without departing from the scope of the invention as defined in the claims that follow.

We claim:

1. An intramedullary fracture fixation device, comprising:
   an intramedullary rod, the rod having distal and proximal ends, the proximal end having a transverse bore extending therethrough;
   a lag screw having distal and proximal ends, the distal end having one or more coarse bone-engaging elements, at least a portion of the lag screw other than the distal end having screw threads, the lag screw being substantially axially aligned with the transverse bore of the rod when in use; and
   a lag screw collar having an outer diameter sized to rotatably fit within the transverse bore of the rod, the collar having an inner diameter and internal screw threads adapted to cooperate with the screw threads of the lag screw.

2. The device according to claim 1, wherein the outer diameter of the collar is sized to substantially abut an inner wall of the transverse bore of the rod such that the collar acts as a centering device for the lag screw relative to the transverse bore.

3. The device according to claim 1, wherein the collar includes at least one flattened outer engagement surface.

4. The device according to claim 3, wherein the collar includes a plurality of circumferentially spaced flattened outer engagement surfaces.

5. The device according to claim 1, wherein the collar includes at least one engagement groove formed on an outer surface thereof.

6. The device according to claim 5, wherein the collar includes a plurality of circumferentially spaced engagement grooves formed on an outer surface thereof.

7. The device according to claim 1, further comprising:
   a longitudinal bore extending through the proximal end of the rod so as to open into the transverse bore, the longitudinal bore being angularly offset with respect to a longitudinal axis of the proximal end of the rod.

8. An intramedullary fracture fixation device, comprising:
   an intramedullary rod, the rod having distal and proximal ends, the proximal end having a transverse bore extending therethrough;
   a lag screw having distal and proximal ends, the distal end having one or more coarse bone-engaging elements, at least a portion of the lag screw other than the distal end having screw threads, the lag screw being substantially axially aligned with the transverse bore of the rod when in use; and
   a lag screw collar having an outer diameter over at least a portion thereof which is sized to rotatably fit within the transverse bore of the rod and an increased outer diameter at one end thereof which is at least slightly larger than a diameter of the transverse bore of the rod, the collar having an inner diameter and internal screw threads adapted to cooperate with the screw threads of the lag screw.

9. The device according to claim 8, wherein the outer diameter of the collar is sized to substantially abut an inner wall of the transverse bore of the rod such that the collar acts as a centering device for the lag screw relative to the transverse bore.

10. The device according to claim 8, wherein the collar includes at least one flattened outer engagement surface.

11. The device according to claim 10, wherein the collar includes a plurality of circumferentially spaced flattened outer engagement surfaces.

12. The device according to claim 8, wherein the collar includes at least one engagement groove formed on an outer surface thereof.

13. The device according to claim 12, wherein the collar includes a plurality of circumferentially spaced engagement grooves formed on an outer surface thereof.

14. The device according to claim 8, further comprising:

a longitudinal bore extending through the proximal end of the rod so as to open into the transverse bore of the rod, the longitudinal bore being angularly offset with respect to a longitudinal axis of the proximal end of the rod.

15. An intramedullary fracture fixation device, comprising:

an intramedullary rod, the rod having distal and proximal ends;

a transverse bore extending through the proximal end of the rod; and a longitudinal bore extending through the proximal end of the rod so as to open into the transverse bore of the rod, the longitudinal bore being angularly offset with respect to a longitudinal axis of the proximal end of the rod.

16. The device according to claim 15, further comprising:

a collar having an outer diameter sized to fit within the transverse bore of the rod; and a set screw which is adapted to be secured within the longitudinal bore of the rod with a distal end thereof extending at least partially into the transverse bore of the rod so as to engage the collar when the collar is disposed within the transverse bore.

17. The device according to claim 16, wherein the collar includes at least one flattened outer engagement surface, the set screw being adapted to engage the engagement surface so as to prevent rotation of the collar within the transverse bore of the rod.

18. The device according to claim 17, wherein the collar includes a plurality of circumferentially spaced flattened outer engagement surfaces, the set screw being adapted to engage any one of the engagement surfaces so as to prevent rotation of the collar within the transverse bore of the rod.

19. The device according to claim 16, wherein the collar includes at least one engagement groove formed on an outer surface thereof, the set screw being adapted to engage the engagement groove so as to prevent rotation of the collar within the transverse bore of the rod.

20. The device according to claim 19, wherein the collar includes a plurality of circumferentially spaced engagement grooves formed on an outer surface thereof, the set screw being adapted to engage any one of the engagement grooves so as to prevent rotation of the collar within the transverse bore of the rod.

* * * * *